United States Patent
Yuan et al.

(10) Patent No.: US 11,446,231 B2
(45) Date of Patent: Sep. 20, 2022

(54) ORAL CARE COMPOSITIONS AND METHODS FOR THE SAME

(71) Applicant: Colgate-Palmolive Company, New York, NY (US)

(72) Inventors: Shaotang Yuan, East Brunswick, NJ (US); Guofeng Xu, Plainsboro, NJ (US); Junhong Mao, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/715,237

(22) Filed: Dec. 16, 2019

(65) Prior Publication Data

US 2020/0206123 A1 Jul. 2, 2020

Related U.S. Application Data

(60) Provisional application No. 62/785,079, filed on Dec. 26, 2018.

(51) Int. Cl.

| | | |
|---|---|---|
| *A61K 8/91* | (2006.01) | |
| *A61Q 11/00* | (2006.01) | |
| *A61K 8/04* | (2006.01) | |
| *A61K 8/34* | (2006.01) | |
| *A61K 8/37* | (2006.01) | |
| *A61K 8/81* | (2006.01) | |
| *A61K 8/86* | (2006.01) | |
| *A61K 8/90* | (2006.01) | |

(52) U.S. Cl.
CPC ............... *A61K 8/91* (2013.01); *A61K 8/042* (2013.01); *A61K 8/345* (2013.01); *A61K 8/375* (2013.01); *A61K 8/817* (2013.01); *A61K 8/8135* (2013.01); *A61K 8/86* (2013.01); *A61K 8/90* (2013.01); *A61Q 11/00* (2013.01); *A61K 2800/48* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 8,632,763 B2 | 1/2014 | Bouillo et al. | |
| 2004/0120900 A1* | 6/2004 | Arsenault | A61K 8/66 424/50 |
| 2008/0081023 A1* | 4/2008 | Deckner | A61K 8/731 424/49 |
| 2013/0157963 A1 | 6/2013 | Gore et al. | |
| 2018/0168969 A1 | 6/2018 | Yuan et al. | |
| 2018/0168972 A1 | 6/2018 | Yuan et al. | |
| 2018/0305636 A1* | 10/2018 | Kolter | A61K 8/34 |
| 2019/0350876 A1 | 11/2019 | Hammell et al. | |

FOREIGN PATENT DOCUMENTS

| | | | |
|---|---|---|---|
| CN | 105769753 | 7/2016 | |
| WO | 2013/191668 | 12/2013 | |
| WO | WO-2017067841 A1 * | 4/2017 | C11D 3/3776 |

OTHER PUBLICATIONS

CN105769753, Univ Zhejiang Technology, "Temperature-sensitive gel matrix and preparation method and application thereof," Jul. 20, 2016, English language machine translation of abstract, Espacenet, date obtained: Jun. 24, 2020, 1 page <https://worldwide.espacenet.com/patent/search/family/056396946/publication/CN105769753A?q=CN105769753A>.

Cespi et al., "Rheological Characterization of Polyvinyl Caprolactam-Polyvinyl Acetate-Polyethylene Glycol graft copolymer (Soluplus) Water Dispersions", Colloid & Polymer Science, 292(1):235-241 (2013).

* cited by examiner

*Primary Examiner* — Brian Gulledge

(57) ABSTRACT

An oral care composition and methods for preparing the oral care composition are disclosed. The oral care composition may include a carrier and a structure-building agent. The carrier may be present in an amount of from about 0.01 wt % to about 99 wt %. The structure-building agent may include a polyvinyl capralactam-polyvinyl acetate-polyethylene glycol graft copolymers (PCA-PVA-PEG), and may be present in an amount of from about 0.01 wt % to about 60 wt %, based on a total weight of the oral care composition.

14 Claims, No Drawings

ORAL CARE COMPOSITIONS AND METHODS FOR THE SAME

CROSS-REFERENCE TO RELATED APPLICATIONS

This application claims priority to U.S. Provisional Patent Application No. 62/785,079, filed Dec. 26, 2018, which is incorporated herein by reference in its entirety.

BACKGROUND

Structure-building agents, also referred to as gelling agents, thickening agents, or thickeners, are often utilized in oral care compositions to increase the viscosity thereof and to provide a structure to hold other components and ingredients of the oral care composition in a homogenous state or in a chemically and/or physically stable environment.

Structure-building agents may be hydrophilic or hydrophobic. Conventional hydrophilic structure-building agents (e.g., polyvinylpyrrolidone (PVP), Carbopol, etc.) may be used to provide a homogenous structure for oral care compositions, and conventional hydrophobic structure-building agents (e.g., plastic gels) may be utilized in oral care compositions for containing relatively large amounts of a hydrophobic oil (e.g., mineral oil). Conventional structure-building agents, however, are not able to provide a homogenous or heterogeneous gel when the oral care composition or a carrier thereof includes low amounts of water (e.g., less than 10 weight %).

What is needed, then, are improved structure-building agents and methods for preparing stable homogenous or heterogeneous oral care compositions.

BRIEF SUMMARY

This section is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition including a carrier and a structure-building agent. The carrier may be present in an amount of from about 0.01 wt % to about 99 wt %, based on a total weight of the oral care composition. The structure-building agent may be present in an amount of from about 0.01 wt % to about 60 weight %, based on a total weight of the oral care composition. In at least one implementation, the structure-building agent may include a polyvinyl capralactam-polyvinyl acetate-polyethylene glycol graft copolymers (PCA-PVA-PEG).

In at least one implementation, the carrier may include a non-aqueous liquid including one or more of glycerin monoacetate, glycerin diacetate triacetin, diethylene glycol diacetate, ethylene glycol diacetate, propylene glycol diacetate (PGDA), or combinations thereof. In one example, the carrier may include a non-aqueous liquid selected from the group consisting of glycerin monoacetate, glycerin diacetate triacetin, diethylene glycol diacetate, ethylene glycol diacetate, propylene glycol diacetate (PGDA), and combinations thereof.

In at least one implementation, the carrier may include a liquid poloxamer or a paste poloxamer.

In at least one implementation, the structure-building agent may consists essentially of the polyvinyl capralactam-polyvinyl acetate-polyethylene glycol graft copolymers. In another implementation, the structure-building agent may only include or consist of the polyvinyl capralactam-polyvinyl acetate-polyethylene glycol graft copolymers.

In at least one implementation, the carrier may include one or more of triacetin, water, propylene glycol, polyethylene glycol 600, glycerin, dimethyl isosorbide, sorbitol, poly(ethylene glycol)-block-poly(propylene glycol)-block-poly(ethylene glycol), or mixtures thereof.

In at least one implementation, the oral care composition may further include one or more of a whitening agent, a surfactant, an antioxidant, a flavoring, a sweetener, a pH modifiers, an abrasive, an anticalculus agent, a source of fluoride ions, a stannous ion source, a colorant, a dye, a pigment, or combinations thereof.

In at least one implementation, the oral care composition is a gel. For example, a heterogenous gel or a homogenous gel.

In at least one implementation, the carrier may include water, wherein water is present in the carrier in an amount of less than 10 weight %, based on a total weight of the oral care composition.

In at least one implementation, the carrier is present in an amount of from about 30 weight % to about 70 weight %, the structure-building agent may be present in an amount of from about 30 weight % to about 70 weight %, and the carrier may include one or more of water, propylene glycol, polyethylene glycol 600, triacetin, or combinations thereof.

In at least one implementation, the oral care composition is a homogenous gel.

In at least one implementation, the carrier may include one or more of glycerin, sorbitol, poly(ethylene glycol)-block-poly(propylene glycol)-block-poly(ethylene glycol), or combinations thereof.

In at least one implementation, the oral care composition may be a heterogeneous gel.

The foregoing and/or other aspects and utilities embodied in the present disclosure may be achieved by providing a personal care composition including a method for preparing any one or more of the oral care compositions disclosed herein. The method may include contacting the carrier and the structure-building agent with one another.

In at least one implementation, the oral care composition is a heterogeneous gel. In another implementation, the oral care composition is a homogenous gel.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any implementations or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

Oral care compositions disclosed herein may include one or more structure-building agents and one or more carriers. The oral care composition including the one or more structure-building agents and the one or more carriers may be a liquid, a gel, or a paste. In at least one implementation, the oral care composition including the one or more structure-building agents and the one or more carriers is a gel. The structure-building agents may be mixed, combined, agitated, reacted, or otherwise contacted with the carriers to prepare the oral care composition. In at least one implementation, the structure-building agents and the carriers may be contacted with one another to prepare the oral care composition in the form of a gel.

In at least one implementation, the oral care composition prior to use may be non-aqueous. For example, the oral care composition may be free of water, substantially free of water, or have a low water content. As used herein, "free of water" or "substantially free of water" may refer to a composition that contains water in an amount of less than 10 weight %, less than 8 weight %, less than 5 weight %, less than 3 weight %, less than 1 weight %, less than 0.1 weight %, less than 0.05 weight %, less than 0.01 weight %, less than 0.005 weight %, or less than 0.0001 weight %, based on a total weight of the oral care composition. In another implementation, the oral care composition prior to use may have a "low water content". As used herein, "low water content" may refer to a composition that contains water in an amount greater than about 5 weight % or greater than about 10 weight %, and less than about 20 weight %, less than about 15 weight %, or less than about 10 weight %.

In at least one implementation, the oral care composition is homogenous. As used herein, the term or expression "homogenous" may refer to a mixture or solution composed of or including two or more compounds, elements, substances, or the like, that are uniformly dispersed into one another. A homogenous oral care composition may be capable of maintaining or exhibiting no phase separation after aging for at least 12 hours, at least 24 hours, at least 36 hours, at least 2 days, at least 3 days, at least 5 days, at least 10 days, at least 15 days, at least 20 days, at least 30 days, at least 2 months, at least 3 months, at least 5 months, at least 6 months, or at least 1 year. In another implementation, the oral care composition is heterogeneous. As used herein, the term or expression "heterogeneous" may refer to any mixture or solution composed of or including two or more compounds, elements, substances, or the like, that may be separated mechanically into their components, regardless of whether they are uniformly dispersed. A heterogeneous oral care composition may exhibit phase separation after aging for at least 12 hours, at least 24 hours, at least 36 hours, at least 2 days, at least 3 days, at least 5 days, at least 10 days, at least 15 days, at least 20 days, at least 30 days, at least 2 months, at least 3 months, at least 5 months, at least 6 months, or at least 1 year. Aging of the oral care composition may be conducted at a temperature of about 0° C., about 1° C., about 25° C., about 35° C., about 45° C., about 49° C., or about 50° C.

Carriers

The one or more carriers may be a liquid, a solid, a paste, or a gel. The carrier may be or include, one or more aqueous dispersants, one or more non-aqueous dispersants, or any combination thereof. For example, the oral care composition may include one or more structure-building agents and one or more non-aqueous dispersants. In another example, the oral care composition may include one or more structure-building agents and one or more aqueous dispersants. In yet another example, the oral care composition may include one or more structure-building agents, one or more non-aqueous dispersants, and one or more aqueous dispersants.

The aqueous dispersant of the carrier may include an aqueous liquid. As used herein, the term or expression "aqueous" or "aqueous liquid" may refer to a substance or mixture of substances that has a moisture or water content of greater than or equal to 1 weight %, greater than or equal to 5 weight %, greater than or equal to 6 weight %, greater than or equal to 8 weight %, or greater than or equal to 10 weight %. Illustrative aqueous liquids may be or include, but are not limited to, water, or solutions or mixtures including at least 10 weight % of water.

In at least one implementation, the aqueous dispersant of the carrier may be present in the oral care composition in an amount of from about 0.01 weight % to about 99 weight %, based on a total weight of the oral care composition. For example, the aqueous dispersant may be present in the oral care composition in an amount of from about 0.01 weight %, about 0.1 weight %, about 0.5 weight %, about 1 weight %, about 5 weight %, about 10 weight %, about 20 weight %, about 30 weight %, about 40 weight % or about 50 weight % to about 55 weight %, about 70 weight %, about 80 weight %, about 90 weight %, about 95 weight %, or about 99 weight %, based on a total weight of the oral care composition.

The non-aqueous dispersant of the carrier may include a non-aqueous liquid. As used herein, the term or expression "non-aqueous" or "non-aqueous liquid" may refer to a substance or mixture of substances that has a moisture or water content of less than or equal to 10 weight %, less than or equal to 8 weight %, less than or equal to 6 weight %, less than or equal to 5 weight %, or less than or equal to 1 weight %, by total weight of the oral care composition. In at least one implementation, the oral care composition includes a non-aqueous dispersant. The non-aqueous dispersant may be sufficiently hydrophilic to react in an aqueous environment or with an aqueous substance.

In at least one implementation, the non-aqueous dispersant of the carrier may be present in the oral care composition in an amount of from about 0.01 weight % to about 99 weight %, based on a total weight of the oral care composition. For example, the non-aqueous dispersant may be present in the oral care composition in an amount of from about 0.01 weight %, about 0.1 weight %, about 0.5 weight %, about 1 weight %, about 5 weight %, about 10 weight %, about 20 weight %, about 30 weight %, about 40 weight % or about 50 weight % to about 55 weight %, about 70 weight %, about 80 weight %, about 90 weight %, about 95 weight %, or about 99 weight %, based on a total weight of the oral care composition.

In at least one implementation, the non-aqueous dispersant of the carrier may be or include a poloxamer. The poloxamer may be a liquid or a paste. The poloxamer may have an average molecular weight of less than or equal to about 12,000 Dalton (Da), less than or equal to about 11,000 Da, less than or equal to about 10,000 Da, less than or equal to about 9,000 Da, less than or equal to about 8,000 Da, less than or equal to about 7,000 Da, or less than or equal to about 6,000 Da. Illustrative poloxamers may be or include, but are not limited to, one or more of PLURONIC® L35 (Poly(ethylene glycol)-block-poly(propylene glycol)-block-poly(ethylene glycol)), PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, and PLURONIC® P105, or the like, or any mixture or combination thereof, each of which or commercially available from BASF Corp. of Florham Park, N.J.

In at least one implementation, the non-aqueous dispersant of the carrier may be or include one or more hydrophobic non-aqueous liquids. Illustrative hydrophobic non-aqueous liquids may be or include, but are not limited to, triacetin, diacetin, propylene glycol diacetate, liquid fatty acids esters, liquid fatty alcohols, mineral oil, or the like, or any combination thereof. In at least one implementation, the one or more hydrophobic non-aqueous liquids may include any one or more of triacetin, diacetin, propylene glycol diacetate, liquid fatty acids esters, liquid fatty alcohols, mineral oil, or the like, or any combination thereof. In another implementation, the one or more hydrophobic non-aqueous liquids may include any one or more of triacetin, diacetin, propylene glycol diacetate, or the like, or any combination thereof. For example, the one or more hydrophobic non-aqueous liquids may exclude, be free, or substantially free of any one or more of liquid fatty acid esters, liquid fatty alcohols, mineral oil, or combinations thereof. In another implementation, the non-aqueous dispersant may be or include one or more hydrophilic non-aqueous liquids. Illustrative hydrophilic non-aqueous liquids may be or include, but are not limited to, glycerin, propylene glycol, ethylene glycols, polyethylene glycol, or the like, or any combination thereof.

Illustrative carriers of the oral care composition may be or include, but are not limited to, one or more of glycerin monoacetate, triacetin, diethylene glycol diacetate, ethylene glycol diacetate, propylene glycol diacetate (PGDA), water, propylene glycol (PG), polyethylene glycol (PEG) (e.g., PEG 400, PEG 600, etc.), glycerin, ethanol, sorbitol (e.g., 30% solution of sorbitol), pluronic L35, polyethylene/polypropylene glycol copolymers (e.g., PEG/PPG 38/8, PEG/PPG-116/66, etc.), or the like, or any combination thereof. In at least one implementation, the carriers of the oral care composition may include any one or more of glycerin monoacetate, triacetin, diethylene glycol diacetate, ethylene glycol diacetate, propylene glycol diacetate (PGDA), water, propylene glycol (PG), polyethylene glycol (PEG) (e.g., PEG 400, PEG 600, etc.), glycerin, ethanol, sorbitol (e.g., 30% solution of sorbitol), pluronic L35, polyethylene/polypropylene glycol copolymers (e.g., PEG/PPG 38/8, PEG/PPG-116/66, etc.), or the like, or any combination thereof. In another implementation, the carriers of the oral care composition may include any one or more of glycerin monoacetate, triacetin, diethylene glycol diacetate, ethylene glycol diacetate, propylene glycol diacetate (PGDA), water, propylene glycol (PG), polyethylene glycol (PEG) (e.g., PEG 400, PEG 600, etc.), glycerin, sorbitol (e.g., 30% solution of sorbitol), pluronic L35, polyethylene/polypropylene glycol copolymers (e.g., PEG/PPG 38/8, PEG/PPG-116/66, etc.), dimethyl isosorbide, or the like, or any combination thereof. For example, the carrier may exclude, be free, or substantially free of ethanol.

The carrier, such as a liquid carrier, may be present in the oral care composition in an amount of from about 0.01 weight % to about 99 weight %, based on a total weight of the oral care composition. For example, the carrier may be present in the oral care composition in an amount of from about 0.01 weight %, about 0.1 weight %, about 0.5 weight %, about 1 weight %, about 5 weight %, about 10 weight %, about 20 weight %, about 30 weight %, about 40 weight % or about 50 weight % to about 55 weight %, about 70 weight %, about 80 weight %, about 90 weight %, about 95 weight %, or about 99 weight %, based on a total weight of the oral care composition. In another example, the carrier may be present in an amount of from about 0.01 weight % to about 99 weight %, about 0.1 weight % to about 95 weight %, about 0.5 weight % to about 90 weight %, about 1 weight % to about 80 weight %, about 5 weight % to about 70 weight %, about 10 weight % to about 55 weight %, about 20 weight % to about 50 weight %, or about 30 weight % to about 40 weight %, based on a total weight of the oral care composition.

Structure-Building Agent

As used herein, the term or expression "structure-building agent" may refer to a substance, component, material, or combination of one or more thereof that may thicken an oral care composition and maintain the oral care composition in a homogenous or heterogeneous state. For example, the structure-building agent may be capable of or configured to hold, interact, maintain one or more ingredients or components of the oral care composition, such as the components of the carrier or carriers, in a homogenous or heterogeneous state. For example, the structure-building agent may be capable of or configured to maintain the oral care composition in a homogenous or a heterogeneous state. The structure-building agent may also be capable of or configured to hold, interact, maintain one or more ingredients or components of the oral care composition, such as the components of the carrier or carriers, in a chemically and/or physically stable state or environment. The structure-building agent may also be capable of or configured to create a stable, homogenous gel with the carrier or carriers of the oral care composition. For example, a stable, transparent or semi-transparent gel may be prepared by combining the structure-building agent and the carrier or carriers.

The structure-building agents may be or include one or more polyvinyl capralactam-polyvinyl acetate-polyethylene glycol graft copolymers (PCA-PVA-PEG). The PCA-PVA-PEG may be or include a polymer including at least one capralactam block, at least one polyvinyl acetate block, and at least one polyethylene glycol block, where at least one block is coupled with or branches from another of the type of blocks. For example, the one or more PCA-PVA-PEG may be represented by formula (1):

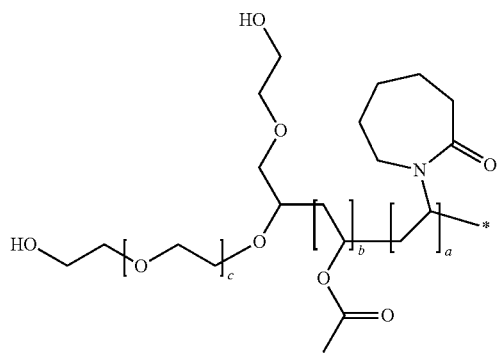

where:

a may be an integer from about 10, about 100, about 200, about 500, or about 1,000 to about 1,200, about 1,500, about 2,000, about 3,000, about 5,000, about 8,000, about 10,000, or greater.

b may be an integer from about 20, about 100, about 200, about 300, about 400, about 500, about 600, or about 700 to about 800, about 900, about 1,000, about 1,100, about 1,200, about 1,300, about 1,400, about 1,500, or greater;

c may be an integer from about 30, about 100, about 500, about 1,000, about 2,000, about 5,000, about 10,000, or about 15,000 to about 16,000, about 18,000, about 20,000, about 22,000, about 25,000, about 28,000, or about 30,000.

The PCA-PVA-PEG may have an average molecular weight of from about 1,000 g/mol, about 2,000 g/mol, about 5,000 g/mol, about 10,000 g/mol, about 50,000 g/mol, about 100,000 g/mol, about 200,000 g/mol, about 300,000 g/mol, about 400,000 g/mol, or about 500,000 g/mol to about 1,000,000 g/mol, about 1,500,000 g/mol, about 2,000,000 g/mol, about 2,500,000 g/mol, about 3,000,000 g/mol, about 3,500,000 g/mol, about 4,000,000 g/mol, about 4,500,000 g/mol, about 5,000,000 g/mol, or greater.

In an exemplary implementation, the PCA-PVA-PEG may be or include a polymer represented by CAS No. 402932-23-4. For example, in at least one implementation, the PCA-PVA-PEG may be or include SOLUPLUS®, which is commercially available from BASF Corp. of Florham Park, N.J.

As discussed above, the oral care composition including the one or more structure-building agents and the one or more carriers is a gel. In at least one implementation, the structure-building agent may be capable of or configured to form a gel or a gel structure via self-assembly. For example, the structure-building agent may be capable of or configured to form a gel with the other structure-building agents and/or the one or more carriers by interacting with the other structure-building agents and/or the one or more carriers via any one or more intermolecular forces (e.g., van der Waal, dipole-dipole, hydrogen bonding, covalent bonding, etc.).

The one or more structure-building agents may be present in the oral care composition in an amount of from about 0.01 weight % to about 99 weight %, based on a total weight of the oral care composition. For example, the one or more structure-building agents may be present in the oral care composition in an amount of from about 0.01 weight %, about 0.1 weight %, about 0.5 weight %, about 1 weight %, about 5 weight %, about 10 weight %, about 20 weight %, about 30 weight %, about 40 weight % or about 50 weight % to about 55 weight %, about 70 weight %, about 80 weight %, about 90 weight %, about 95 weight %, or about 99 weight %, based on a total weight of the oral care composition. In another example, the one or more structure-building agents may be present in an amount of from about 0.01 weight % to about 99 weight %, about 0.1 weight % to about 95 weight %, about 0.5 weight % to about 90 weight %, about 1 weight % to about 80 weight %, about 5 weight % to about 70 weight %, about 10 weight % to about 55 weight %, about 20 weight % to about 50 weight %, or about 30 weight % to about 40 weight %, based on a total weight of the oral care composition.

The structure-building agents and the carriers may be present in a weight ratio of from about 100:1 to about 1:100. For example, a weight ratio of the structure-building agent to the carrier or the carrier to the structure-building agent may be from about 100:1, about 90:1, about 80:1, about 70:1, about 60:1, about 50:1, about 40:1, about 30:1, about 20:1, about 10:1, about 5:1, about 1:1, about 1:2, about 1:5, about 1:10, about 1:20, about 1:30, about 1:40, about 1:50, about 1:60, about 1:70, about 1:80, about 1:90, or about 1:100. In another example, a weight ratio of the structure-building agent to the carrier or the carrier to the structure-building agent may be from about 100:1 to about 1:100, about 90:1 to about 1:90, about 80:1 to about 1:80, about 70:1 to about 1:70, about 60:1 to about 1:60, about 50:1 to about 1:50, about 40:1 to about 1:40, about 30:1 to about 1:30, about 20:1 to about 1:20, about 10:1 to about 1:10, about 5:1, about 1:5, or about 1:1.

It should be appreciated that viscosity of oral care compositions, such as toothpastes or whitening gels, may be an important parameter or factor. For example, when the viscosity of an oral care composition is too low, it may become too runny and exhibit phase separation. In some instances, this will not only affect the aesthetics of the oral care composition but also the homogeneity of the oral care composition and/or the ingredients/components thereof. Conversely, if the viscosity of the oral care compositions is too high, the oral care composition may be difficult to manufacture and package. Additionally, oral care compositions having a high viscosity are often difficult for users and consumers to dispense from commonly used packages, such as tubes or syringes. In some implementations, the gel formed from the structural-building agent and the carrier may at least partially determine the overall viscosity of the oral care composition. Accordingly, it should be appreciated that the selection of the ingredients or components of the oral care composition (e.g., the structural-building agent and the carrier) is important to achieve a desired viscosity or range of viscosity to thereby enable sufficient and satisfactory product manufacturability, product stability, product quality, and consumer acceptance.

In at least one implementation, the viscosity of the oral care composition may be from about 5,000 centipoise (cP) to about 700,000 cP, as measured at about 25° C. For example, the viscosity of the oral care composition, measured at about 25° C., may be from about 5,000 cP, about 10,000 cP, about 15,000 cP, about 25,000 cP, about 50,000 cP, about 75,000 cP, about 100,000 cP, or about 125,000 cP to about 150,000 cP, about 175,000 cP, about 200,000 cP, about 300,000 cP, about 400,000 cP, about 450,000 cP, about 500,000 cP, about 550,000 cP, about 600,000 cP, about 650,000 cP, about 700,000 cP, or about 750,000 cP.

Additional Ingredients

The oral care compositions disclosed herein may include additional and/or optional ingredients or components. For example, the oral care compositions may include any one or more of additional dispersants, desensitizing agents, viscosity modifiers, surfactants, diluents, surface active agents (e.g., emulsifiers, foam modulators, etc.), whitening agents, pH modifying agents (e.g., acids and bases), humectants, tartar control agents, mouth feel agents, sweeteners or sweetening agents, flavor or flavoring agents, colorants, dyes, pigments, preservatives, or the like, or combinations and mixtures thereof. It should be appreciated by one having ordinary skill in the art that while general attributes of each of the above categories of ingredients or components may differ, there may be some common attributes and any given material may serve multiple purposes within two or more of such categories of materials.

As discussed above, the oral care composition may include one or more whitening agents. As used herein, the expression "whitening agent" may refer to a material that affects the whitening of a tooth surface to which it is applied. Any whitening agent known or developed in the art may be used in the present oral care composition.

For example, in some implementations, the whitening agent may be or include a whitening pigment. In some implementations, the whitening pigments include particles ranging in size from about 0.1 μm to about 10 μm with a refractive index greater than about 1.2. Illustrative whitening agents may be or include, but are not limited to, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles, or combinations thereof. The whitening pigment, such as titanium dioxide particles, may be in an amount that is sufficient to whiten the teeth.

In some implementations, the whitening agent may be or include, but are not limited to, an oxidizing agent, a reducing agent, or combinations thereof. As used herein, the expression "oxidizing agent" may refer to material and/or compounds that can accept an electron from another material and/or compound (e.g., molecule) in the environment of the oral cavity without having a deleterious or unacceptably harmful effect on the oral cavity in normal and accepted use. Illustrative oxidizing agents suitable for use with the oral care composition may include, but are not limited to, peroxides, chlorites and hypochlorites. Examples of suitable chlorites and hypochlorites include those having alkali or alkaline metal cations and include calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

In at least one implementation, the whitening agent may include a peroxide compound. As used herein, the expression "peroxide compound" may refer to any compound including a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and mixtures thereof. Peroxy acids and their salts include organic peroxy acids, such as alkyl peroxy acids and monoperoxyphthalate and mixtures thereof, as well as inorganic peroxy acid salts, such as persulfate, dipersulfate, percarbonate, perphosphate, perborate and persilicate salts of alkali and alkaline earth metals such as lithium, potassium, sodium, magnesium, calcium and barium, and mixtures thereof. Typically, the peroxide compound comprises hydrogen peroxide, urea peroxide, sodium percarbonate or mixtures thereof.

In at least one implementation, the whitening agent may include a non-peroxide whitening agent, such as chlorine dioxide, chlorites, and hypochlorites. Chlorites and hypochlorites include those of alkali and alkaline earth metals such as lithium, potassium, sodium, magnesium, calcium and barium. Non-peroxide whitening agents also include colorants, such as titanium dioxide, and hydroxyapatite.

In at least one implementation, the whitening agent may be or include, but is not limited to, a whitening complex. As used herein, the expression "whitening complex" may refer to a whitening agent as described herein complexed with a polymer or copolymer that is capable of or configured to release the whitening agent upon exposure to highly aqueous environments, such as in the oral cavity. As used herein, a "complex" is an entity formed by a loose association involving two or more molecular entities (ionic or uncharged), e.g., a whitening agent and a polymer.

The whitening agent may be present in the oral care composition in an amount of from about 0.01 weight % to about 50 weight %, based on a total weight of the oral care composition. For example, the oral care composition may include any one or more of the whitening agents in an amount of from about 0.01 weight %, about 0.05 weight %, about 0.1 weight %, about 0.5 weight %, about 1 weight %, about 2 weight %, or about 3 weight % to about 4 weight %, about 5 weight %, about 8 weight %, about 10 weight %, about 12 weight %, about 15 weight %, about 20 weight %, about 25 weight %, or about 50 weight %, based on a total weight of the oral care composition.

In at least one implementation, the oral care composition includes one or more surfactants. In some implementations, the surfactants may enhance the stability of the oral care composition, help clean the oral cavity surfaces through detergency, provide foam upon agitation (e.g., during brushing with an oral care composition of the disclosure), or any combination thereof. Surfactants or surface active agents may generally achieve increased whitening action by thoroughly dispersing the whitening agent throughout the oral cavity. In various implementations, suitable surfactants or surface active agents may function as a surface active agent, emulsifier, and/or foam modulator. The surfactants may be or include anionic, nonionic, cationic, amphoteric surfactants, or combinations thereof.

Illustrative surfactants may be or include, but are not limited to, water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate, and sodium dodecyl benzenesulfonate, and cocoamidopropyl betaine. Illustrative surfactants or surface active agents may also be or include, but are not limited to, PLURONIC® L35, PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, PLURONIC® P105, and the like, and combinations thereof, which are commercially available from BASF of Florham Park, N.J. In a typical implementation, the surfactant is or includes a poly(ethylene glycol)-block-poly(propylene glycol)-block-poly(ethylene glycol) or PEG-PPG-PEG (PLURONIC® L-35).

Illustrative anionic surfactants may also be or include, but are not limited to, sodium lauryl sulfate, sodium cocoyl monoglyceride sulfonate, sodium lauryl sarcosinate, sodium lauryl isoethionate, sodium laureth carboxylate, and sodium dodecyl benzenesulfonate.

Illustrative nonionic surfactants may include, but are not limited to, poloxamers, polyoxyethylene sorbitan esters, fatty alcohol ethoxylates, alkylphenol ethoxylates, tertiary amine oxides, tertiary phosphine oxides, dialkyl sulfoxides, or the like, or any combination thereof. For example, the nonionic surfactants may include polysorbate 20, poloxamer 407, poloxamer 338, or the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred implementation, the nonionic surfactant is polysorbate 20.

Illustrative amphoteric and zwitterionic surfactants may be or include, but are not limited to, derivatives of C8-20 aliphatic secondary and tertiary amines having an anionic group such as carboxylate, sulfate, sulfonate, phosphate or phosphonate. Illustrative amphoteric and zwitterionic surfactants may include cocamidopropyl betaine (CAP betaine).

The amount of any one or more of the surfactants in the oral care composition may be from about 0.01 wt % to about 20 weight %, based on a total weight of the oral care composition. For example, the amount of any one or more of the surfactants in the oral care composition may be from about 0.01 weight %, about 0.020 wt %, about 0.030 wt %, about 0.040 wt %, about 0.045 wt %, about 0.049 wt %, or about 0.050 wt % to about 0.051 wt %, about 0.055 wt %, about 0.060 wt %, about 0.065 wt %, about 0.070 wt %, about 0.075 wt %, about 0.080 wt %, or greater.

In at least one implementation, the oral care composition may include one or more additional structure-building agents. For example, the oral care composition may include a cross-linked polymer, such as cross-linked polyvinylpyrrolidone ("PVP") in addition to the PCA-PVA-PEG structure-building agents. In one implementation, the structure-building agent includes one or more cross-linked polymers capable of interacting with the carrier or the dispersants thereof.

Illustrative additional structure-building agents may be or include, but are not limited to, polymer and copolymers, such as N-vinyl lactam based polymers and copolymers. The monomers for preparing a vinyl lactam-based polymer or co-polymer may include any monomer having 3 to 8 atoms in a heterocyclic ring, including a carbonyl carbon atom and a heteroatom (such as N, S, O) in its vinyl moiety. Suitable monomers may include, but not limited, to N-vinyl-2-pyrrolidone, N-vinyl-2-piperidone, N-vinyl-3-methyl-pyrrolidinone, N-vinyl-3-methyl-piperidone, N-vinyl-3-methyl-caprolactam, N-vinyl-4-methyl-pyrrolidinone, N-vinyl-4-methyl-2-pyrrolidone, N-vinyl-4-methyl-piperidone, N-vinyl-4-methyl-caprolactam, N-vinyl-5-methyl-pyrrolidinone, N-vinyl-5-ethyl-2-pyrrolidone, N-vinyl-4-methyl-piperidone, N-vinyl-3-ethyl-pyrrolidinone, N-vinyl-4,5-dimethyl-pyrrolidinone, N-vinyl-5,5-dimethyl-pyrrolidinone, N-vinyl-3,3,5-trimethyl-pyrrolidinone, N-vinyl-5-methyl-5-ethyl-pyrrolidinone, N-vinyl-3,4,5-trimethyl-3-ethyl-pyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methyl-caprolactam, N-vinyl-7-ethyl-caprolactam, N-vinyl-3,5-dimethyl-caprolactam, N-vinyl-4,6-dimethyl-caprolactam, N-vinyl-3,5,7-trimethyl-caprolactam, N-vinyl-2-valerolactam, N-vinyl-hexahydro-2-azepinone, N-vinyl-octahydro-2-azocinone, N-vinyl octahydro-2-azoninone, N-vinyl decahydro-2-azecinone, or combinations thereof.

The polymer may be a cross-linked polyvinylpyrrolidone, also known as poly-N-vinyl-poly-2-pyrrolidone, and commonly abbreviated to cross-linked "PVP." PVP may generally refer to a polymer containing vinylpyrrolidone (also referred to as N-vinylpyrrolidone, N-vinyl-2-pyrrolidione and N-vinyl-2-pyrrolidinone) as a monomeric unit. The monomeric unit may include a polar imide group, four non-polar methylene groups, and a non-polar methane group. Cross linked PVP includes those commercially available as KOLLIDON® and LUVICROSS®, marketed by BASF, Florham Park, N.J.; and POLYPLASDONE® INF-10 of Ashland, Covington, Ky.

In some embodiments, the oral care composition may include one or more thickening agents. Any orally acceptable thickening agents may be utilized. Illustrative thickening agents may be or include, but are not limited to, carbomers, also known as carboxyvinyl polymers, carrageenans, also known as Irish moss, and more particularly carrageenan, high molecular weight polyethylene glycols (e.g., CARBOWAX™, which is commercially available from The Dow Chemical Company), cellulosic polymers such as hydroxyethylcellulose, carboxymethylcellulose ("CMC") and salts thereof, (e.g., CMC sodium), natural gums such as karaya, xanthan, gum Arabic, tragacanth, colloidal magnesium aluminum silicate, or colloidal or fumed silica, or mixtures thereof. The thickening agents may be a combination of one or more orally acceptable thickening agents.

In some implementations, the thickening agent may be present in the oral care composition in an amount of from about 0.01 weight % to about 30 weight %, based on a total weight of the oral care composition. In other implementations, the thickening agent may be present in the oral care composition in an amount of from about 0.1 weight % to about 20 weight %, based on a total weight of the oral care composition. In yet another implementation, the thickening agent may be present in the oral care composition in an amount of from about 0.5 weight % to about 10 weight %, based on a total weight of the oral care composition. For example, the thickening agent (e.g., fumed silica) may be present in the oral care composition in an amount of about 3 weight %.

In some implementations, the oral care composition may include one or more antioxidants. Illustrative antioxidants may be or include, but are not limited to, BHA, BHT, vitamin A, carotenoids, vitamin E, flavonoids, polyphenols, ascorbic acid, herbal antioxidants, chlorophyll, melatonin, or the like, or mixtures or combinations thereof. In some implementations, the antioxidants may be present in the oral care composition in an amount of from about 0.001 weight % to about 1 weight %, based on a total weight of the oral care composition. In at least one implementation, the antioxidants may be present in the oral care composition in an amount of about 0.03 weight %.

The oral care composition may include one or more flavoring agents. Illustrative flavoring agents may be or include, but are not limited to, any material or mixture of materials capable of or configured to enhance the taste of the oral care composition. Any orally acceptable natural or synthetic flavoring agent can be used, such as flavoring oils, flavoring aldehydes, esters, alcohols, similar materials, or combinations thereof. Illustrative flavoring agents may be or include, but are not limited to, vanillin, sage, marjoram, parsley oil, spearmint oil, cinnamon oil, oil of wintergreen (methylsalicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, or mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, *eucalyptus* oil, eucalyptol, anethole, eugenol, *cassia*, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1, 2-diol, cinnamaldehyde glycerol acetal (CGA), methone glycerol acetal (MGA), or mixtures thereof.

The one or more flavoring agents may be present in the oral care composition in an amount of from about 0.01 weight % to about 5 weight %, based on a total weight of the oral care composition. In another implementation, the oral care composition may include from about 0.05 weight % to about 3 weight % of the flavoring agents. In yet another implementation, the oral care composition may include from about 0.1 weight % to about 3 weight %, from about 0.2 weight % to about 2.5 weight %, or about 1.5 weight % of the flavoring agents, based on a total weight of the oral care composition. For example, the oral care composition may include about 1.5 weight % of dental cream flavor.

The oral care composition may include one or more sweeteners. The sweeteners may be or include orally acceptable natural or artificial, nutritive or non-nutritive sweeteners. Illustrative sweeteners may be or include, but are not limited to, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, or mixtures thereof. In some implementations, the oral care composition may include from about 0.005% to about 5% of the sweeteners, based on a total weight of the oral care composition. In other implementation, the oral care composition may include from about 0.01% to about 1% of the sweeteners. For example, the oral care composition may include about 0.5 weight % sodium saccharin and about 0.04 weight % sucralose.

In some implementations, the oral care composition may also include one or more pH modifying agents. The pH modifying agents may include acidifying agents to lower pH, basifying agents to raise pH, and buffering agents to control pH within a desired range. One or more compounds selected from acidifying, basifying and buffering agents can be included to provide a pH of 2 to 10, or in various embodiments from about 2 to about 8, from about 3 to about 9, from about 4 to about 8, from about 5 to about 7, from about 6 to about 10, and from about 7 to about 9. Illustrative pH modifying agent may be or include, but are not limited to, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. The oral care composition may include from about 0.01% to about 10% of the pH modifier agents, based on a total weight of the oral care composition. For example, the oral care composition may include about 0.9 weight % sodium acid pyrophosphate (SAPP) and about 2 weight % tetrasodium pyrophosphate (TSPP).

In some implementations, the oral care composition may also include one or more colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cycl-ohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin), or mixtures thereof.

The oral care compositions may include one or more active ingredients capable of, configured to, or operable for preventing or treating a condition or disorder of hard or soft tissue of the oral cavity, preventing or treating a physiological disorder or condition, or for providing a cosmetic benefit.

The oral care composition may include one or more abrasives, such as dental abrasives, dental abrasive agents, or combinations thereof. As used herein, the term "abrasive"

or "abrasive agent" also includes materials commonly referred to as "polishing agents." Any orally acceptable abrasive can be used, but typically, type, fineness (particle size) and amount of abrasive should be selected so that tooth enamel is not excessively abraded in normal use of the composition. Illustrative abrasives may be or include, but are not limited to, silica (in the form of silica gel, hydrated silica or precipitated silica), alumina, insoluble phosphates, calcium carbonate, resinous abrasives such as urea-formaldehyde condensation products, dicalcium orthophosphate dihydrate, calcium pyrophosphate, n-calcium pyrophosphate, tricalcium phosphate, calcium polymetaphosphate, insoluble sodium polymetaphosphate, or the like, or combinations thereof. Illustrative insoluble phosphates may be or include, but are not limited to, orthophosphates, polymetaphosphates, pyrophosphates, or the like, or combinations thereof.

The oral care composition may include one or more anticalculus agents. Illustrative anticalculus agents may be or include, but are not limited to, phosphates and polyphosphates (e.g., pyrophosphates), tetrasodium pyrophosphate (TSPP), sodium tripolyphosphate (STPP), polyaminopropanesulfonic acid (AMPS), hexametaphosphate salts, zinc citrate trihydrate, polypeptides, polyolefin sulfonates, polyolefin phosphates, diphosphonates, or the like, or combinations thereof. In some embodiments, the anticalculus agent is present in an amount of from about 0.01% to about 30% weight based on the total weight of the oral care composition. In at least one implementation, the anticalculus agent may include from 0.1% to 10 weight % of any one or more of the anticalculus agents.

Another component of the oral care composition may include a synthetic anionic polymeric polycarboxylate, which may act as a stabilizer for the polyphosphate antitartar agent, and which may help to block access of painful or pain-causing materials, such as sugars, to the tooth nerves.

The oral care composition may include one or more fluoride ion sources (e.g., soluble fluoride salts). A wide variety of fluoride ion-yielding materials may employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference in their entirety to the extent they are consistent with the present disclosure. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a preferred implementation, the fluoride ion source includes sodium fluoride. The amount of the fluoride ion source present in the oral care composition may be less than 0.08 wt %. For example, the amount of the fluoride ion source present in the oral care composition may be less than 0.08 weight %, less than 0.07 weight %, less than 0.06 weight %, less than 0.05 weight %, or less than 0.04 weight %. In another implementation, the fluoride ion source is present in an amount to provide fluoride ions in a total amount of about 100 to about 20,000 ppm, about 200 to about 5,000 ppm, or about 500 to about 2,500 ppm.

The oral care composition may include one or more stannous ions or stannous ion sources capable of or configured to mitigate calcium loss. Illustrative stannous ion sources may be or include, but are not limited to, stannous fluoride, other stannous halides, stannous chloride dihydrate, stannous pyrophosphate, organic stannous carboxylate salts stannous formate, stannous acetate, stannous gluconate, stannous lactate, stannous tartrate, stannous oxalate, stannous malonate, and stannous citrate, stannous ethylene glyoxide, or the like, or combinations thereof. The oral care composition may include any one or more of the stannous ions or the stannous ion sources in an amount of from about 0.01% to about 10%, based on the total weight of the oral care composition.

All ingredients for use in the compositions described herein should be orally acceptable. As used herein, "orally acceptable" may refer any ingredient that is present in a composition as described in an amount and form which does not render the composition unsafe for use in the oral cavity.

METHODS

The present disclosure may provide methods for treating one or more conditions of an oral cavity in a human or animal subject in need thereof. As used herein "animal subject" may include higher order non-human mammals such as canines, felines, and horses. The method may include contacting any one of the oral care compositions disclosed herein with surfaces of the oral cavity, such as surfaces of teeth. Contacting the surface of the teeth with the oral care composition may include applying the oral care composition directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, spray, roller ball, or nonwoven pad, or the like. Contacting the surface of the teeth with the oral care composition may also include disposing the oral care composition in a dental tray (e.g., reservoir of a dental tray) and disposing the dental tray about the teeth.

The method may also include evaporating a solvent from the oral care composition to form a film on the surfaces of the teeth. The method may also include maintaining the film on the surfaces of the teeth for at least 12 hours, at least one day, at least two days, at least three days, at least four days, or more.

The method may include applying or contacting the oral care composition with the surfaces of the teeth at predetermined intervals. For example, the method may include applying or contacting the oral care composition with the surfaces of the teeth before, during, and/or after brushing, on a daily basis, every other day, once or twice a week, or once a month. In another example, the method may include applying or contacting the oral care composition with the surfaces of the teeth at least once a day, at least once every two days, at least once every three days, at least once every five days, at least once a week, at least once every two weeks, or at least once a month. The oral care composition may be utilized for up to 2 weeks, up to 3 weeks, up to 4 weeks, up to 6 weeks, up to 8 weeks, or greater.

In some implementations, the oral care composition may be activated and maintained on surfaces of a tooth for about 1 minute to about 8 hours. In some implementations, the oral care composition may be activated and maintained on the surfaces of a tooth for about 5 minutes to about 4 hours. In some implementations, the oral care composition is activated and maintained on the surface of a tooth for from about 10 minutes to about 120 minutes. In some implementations, the oral care composition is activated and maintained on the surface of a tooth for from about 15 minutes to about 60 minutes. In some implementations, the oral care composition is activated and maintained on the surface of a tooth for from about 20 minutes to about 45 minutes.

The present disclosure may further provide methods for preparing any one of the oral care compositions disclosed herein. The method may include mixing, dissolving, combining, or otherwise contacting each component of the oral care compositions with one another. For example, the method may include contacting one or more structure-building agents and one or more carriers with one another. The components or ingredients of the oral care composition may be homogenized via any acceptable mixing technique or method.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The efficacy of a structure-building agents, namely a polyvinyl capralactam-polyvinyl acetate-polyethylene glycol graft copolymers (PCA-PVA-PEG) (SOLUPLUS®), for preparing oral care compositions in the form of a gel was evaluated. Generally, about 30 to about 50 weight % of the PCA-PVA-PEG and about 50 to about 70 weight % of varying carriers (i.e., liquid carrier) were combined with one another via speed mixing. After mixing, each of the gel mixtures were placed in room temperature and evaluated. The results of the study are summarized in Table 1.

TABLE 1

| Sample No. | Structure-Building Agent (wt %) | Carrier (wt %) | Results |
|---|---|---|---|
| 1 | 30 wt % PCA-PVA-PEG | 70 wt % water | Homogenous Gel |
| 2 | 30 wt % PCA-PVA-PEG | 70 wt % propylene glycol | Homogenous Gel |
| 3 | 30 wt % PCA-PVA-PEG | 70 wt % polyethylene glycol 600 | Homogeneous Gel |
| 4 | 30 wt % PCA-PVA-PEG | 70 wt % glycerin | Heterogeneous Gel Phase Separation |
| 5 | 30 wt % PCA-PVA-PEG | 70 wt % ethanol | No Gel Formed |
| 6 | 30 wt % PCA-PVA-PEG | 70 wt % sorbitol (30% soln) | Heterogeneous Gel Phase Separation |
| 7 | 30 wt % PCA-PVA-PEG | 70 wt % triacetin | Homogeneous Gel |
| 8 | 30 wt % PCA-PVA-PEG | 70 wt % pluronic L35 | Heterogeneous Gel Phase Separation |
| 9 | 40 wt % PCA-PVA-PEG | 60 wt % dimethyl isosorbide | Homogeneous gel |
| 10 | 50 wt % PCA-PVA-PEG | 50 wt % dimethyl isosorbide | Homogeneous gel |

As illustrated in Table 1, the PCA-PVA-PEG was able to form a stable, homogenous gel with water, propylene glycol, polyethylene glycol 600, dimethyl isosorbide, and triacetin. Accordingly, the PCA-PVA-PEG was able to form a well structured gel matrix with water, propylene glycol, polyethylene glycol 600, dimethyl isosorbide, and triacetin. As further illustrated in Table1, the PCA-PVA-PEG was able to form heterogeneous gels with glycerin, sorbitol, and pluronic L35. Particularly, the gels formed from the combination of PCA-PVA-PEG and each of glycerin, sorbitol, and pluronic L35 each exhibited phase separation after aging for about 24 hours at room temperature. As further illustrated in Table 1, the PCA-PVA-PEG was not able to form a gel with ethanol, which suggested that the PCA-PVA-PEG does not form a well structured gel matrix with ethanol. Without being bound by theory, it is believed that the PCA-PVA-PEG provides a suitable structure-building agent for preparing a homogenous or heterogeneous gel matrix with at least one of propylene glycol, polyethylene glycol 600, dimethyl isosorbide, triacetin, sorbitol, glycerin, pluronic L35, water, or the like, or any combination thereof. The gel matrix prepared may be utilized as a base for any one or more oral care products or oral care compositions thereof, such as toothpastes, gels for dental trays, leave on gels, as well as other oral product platforms that may utilize a homogenous or heterogeneous gel.

The present disclosure has been described with reference to exemplary embodiments. Although a limited number of embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. An oral care composition, comprising:
   from 30%-70% by wt. of a carrier, based on a total weight of the oral care composition, wherein the carrier is selected from: triacetin, water, propylene glycol, polyethylene glycol 600, glycerin, dimethyl isosorbide, sorbitol, poly(ethylene glycol)-block-poly(propylene glycol)-block-poly(ethylene glycol), and mixtures thereof; and
   from 20%-50% by wt. of a structure-building agent, based on the total weight of the oral care composition, wherein the structure-building agent comprises a polyvinyl capralactam-polyvinyl acetate-polyethylene glycol graft copolymer (PCA-PVA-PEG);
   wherein the oral care composition is a gel.

2. The oral care composition of claim 1, wherein the structure-building agent consists essentially of the polyvinyl capralactam-polyvinyl acetate-polyethylene glycol graft copolymers.

3. The oral care composition of claim 1, further comprising one or more of a whitening agent, a surfactant, an antioxidant, a flavoring, a sweetener, a pH modifiers, an abrasive, an anticalculus agent, a source of fluoride ions, a stannous ion source, a colorant, a dye, a pigment, or combinations thereof.

4. The oral care composition of claim 1, wherein the carrier comprises water, wherein water is present in the carrier in an amount of less than 10 weight %, based on a total weight of the oral care composition.

5. The oral care composition of claim 1, wherein the structure-building agent is present in an amount of from about 30 weight % to about 40 weight %, and wherein the carrier is selected from water, propylene glycol, polyethylene glycol 600, triacetin, and combinations thereof.

6. The oral care composition of claim 1, wherein the oral care composition is a homogeneous gel.

7. The oral care composition of claim 1, wherein the carrier is selected from glycerin, sorbitol, poly(ethylene glycol)-block-poly(propylene glycol)-block-poly(ethylene glycol), and combinations thereof.

8. The oral care composition of claim 1, wherein the oral care composition is a heterogeneous gel.

9. The oral care composition of claim 1, wherein the carrier is present in an amount of about 70% by wt., wherein the carrier is selected from: triacetin, water, propylene glycol, polyethylene glycol 600, glycerin, dimethyl isosorbide, sorbitol, poly(ethylene glycol)-block-poly(propylene glycol)-block-poly(ethylene glycol), and mixtures thereof; and
  wherein the structure-building agent is present in an amount of about 30 weight %, wherein structure-building agent comprises a polyvinyl capralactam-polyvinyl acetate-polyethylene glycol graft copolymer (PCA-PVA-PEG).

10. An oral care composition, comprising:
from 30%-70% by wt. of a carrier, based on a total weight of the oral care composition, wherein the carrier is selected from: glycerin monoacetate, glycerin diacetate triacetin, diethylene glycol diacetate, and ethylene glycol diacetate, and
from 20%-50% by wt. of a structure-building agent, based on the total weight of the oral care composition, wherein the structure-building agent comprises a polyvinyl capralactam-polyvinyl acetate-polyethylene glycol graft copolymer (PCA-PVA-PEG);
wherein the oral care composition is a gel.

11. An oral care composition comprising:
from 30%-70% by wt. of a carrier, based on a total weight of the oral care composition, wherein the carrier is selected from: a liquid poloxamer and a paste poloxamer, and
from 20%-50% by wt. of a structure-building agent, based on the total weight of the oral care composition, wherein the structure-building agent comprises a polyvinyl capralactam-polyvinyl acetate-polyethylene glycol graft copolymer (PCA-PVA-PEG);
wherein the oral care composition is a gel.

12. A method for preparing the oral care composition of claim 1, the method comprising contacting the carrier and the structure-building agent with one another.

13. The method of claim 12, wherein the oral care composition is a heterogeneous gel.

14. The method of claim 12, wherein the oral care composition is a homogenous gel.

* * * * *